(12) United States Patent
Kanda

(10) Patent No.: US 10,176,255 B2
(45) Date of Patent: Jan. 8, 2019

(54) MOBILE TERMINAL, RECOMMENDATION SYSTEM, AND RECOMMENDATION METHOD

(71) Applicant: KYOCERA CORPORATION, Kyoto (JP)

(72) Inventor: Atsuhiko Kanda, Kyoto (JP)

(73) Assignee: KYOCERA CORPORATION, Kyoto (JP)

(*) Notice: Subject to any disclaimer, the term of this patent is extended or adjusted under 35 U.S.C. 154(b) by 371 days.

(21) Appl. No.: 14/835,984

(22) Filed: Aug. 26, 2015

(65) Prior Publication Data

US 2016/0063101 A1    Mar. 3, 2016

(30) Foreign Application Priority Data

Aug. 28, 2014  (JP) .................. 2014-173480

(51) Int. Cl.
  *G06F 17/30*  (2006.01)
  *A61B 5/024*  (2006.01)

(52) U.S. Cl.
  CPC ........ *G06F 17/30749* (2013.01); *A61B 5/024* (2013.01); *A61B 5/02438* (2013.01)

(58) Field of Classification Search
  USPC ......................... 707/736, E17.009
  See application file for complete search history.

(56) References Cited

U.S. PATENT DOCUMENTS

| | | | | |
|---|---|---|---|---|
| 8,672,823 B2* | 3/2014 | Parruca | ............... | B65H 1/26 493/405 |
| 9,449,082 B2* | 9/2016 | Leonard | ............... | H04R 3/04 |
| 2005/0141729 A1* | 6/2005 | Kanzaki | ............... | A61B 5/02438 381/67 |
| 2008/0255430 A1* | 10/2008 | Alexandersson | .. | A61B 5/02055 600/300 |
| 2010/0142720 A1* | 6/2010 | Kon | ............... | H04R 29/00 381/74 |
| 2010/0278318 A1* | 11/2010 | Flockhart | ............... | G10L 17/26 379/88.04 |
| 2011/0021293 A1* | 1/2011 | York | ............... | A63B 71/06 473/407 |

(Continued)

FOREIGN PATENT DOCUMENTS

| | | |
|---|---|---|
| JP | 2005-056205 A | 3/2005 |
| JP | 2013-196647 A | 9/2013 |

OTHER PUBLICATIONS

Official Action dated Nov. 14, 2017, in corresponding Japanese Patent Application No. 2014-173480 with Statement of Relevance of Non-English references.

*Primary Examiner* — Baoquoc N To
(74) *Attorney, Agent, or Firm* — Duane Morris LLP

(57) ABSTRACT

A method and apparatus for recommending content is disclosed. In one embodiment, a mobile terminal, includes: a saving unit in which a plurality of contents is saved; an acquiring unit that acquires a physiological information; a storage unit that stores a database that associates the physiological information with the plurality of contents; an acquiring unit that acquires physiological information; and a recommending unit that, when physiological information has been acquired by the acquiring unit, refers to the database and recommends a specific content from the plurality of contents, on the basis of the physiological information.

11 Claims, 13 Drawing Sheets

(56) References Cited

U.S. PATENT DOCUMENTS

| | | | |
|---|---|---|---|
| 2011/0093415 A1* | 4/2011 | Rhee | G06F 17/30864 706/12 |
| 2012/0245178 A1* | 9/2012 | Su | A61K 31/437 514/249 |
| 2014/0213864 A1* | 7/2014 | Abdul-Hafiz | A61B 5/14552 600/325 |
| 2014/0311209 A1* | 10/2014 | Niederberger | G01K 15/007 73/1.06 |
| 2016/0104486 A1* | 4/2016 | Penilla | H04L 67/12 704/232 |
| 2017/0140757 A1* | 5/2017 | Penilla | G10L 15/22 |
| 2017/0200449 A1* | 7/2017 | Penilla | G10L 15/22 |
| 2017/0340293 A1* | 11/2017 | Al-Ali | A61B 5/7275 |
| 2018/0061415 A1* | 3/2018 | Penilla | G10L 15/22 |

* cited by examiner

PLAY LOG TABLE

| CONTENT | PHYSIOLOGICAL INFORMATION | | | |
|---|---|---|---|---|
| | START | | END | |
| | HEART RATE | STRESS LEVEL | HEART RATE | STRESS LEVEL |
| A | 8 0 bpm | LV. 3 | 1 4 0 bpm | LV. 4 |
| B | 6 0 bpm | LV. 2 | 5 5 bpm | LV. 1 |
| ⋮ | ⋮ | ⋮ | ⋮ | ⋮ |

FIG. 6

PLAY LOG TABLE

| CONTENT | TOTAL PLAY TIME | PLAY PERCENTAGE | PHYSIOLOGICAL INFORMATION ||||| BEHAVIORAL INFORMATION |||||
|---|---|---|---|---|---|---|---|---|---|---|---|
| | | | START || END || START || END || SONG SELECTION |
| | | | HEART RATE | STRESS LEVEL | HEART RATE | STRESS LEVEL | OPERATION MODE | PLAY LOCATION | OPERATION MODE | PLAY LOCATION | |
| A | 10分 | 100% | 80bpm | LV. 3 | 140bpm | LV. 4 | WALK | PARK | RUN | PARK | NO |
| C | 5分 | 1% | 60bpm | LV. 2 | 60bpm | LV. 2 | STOP | HOME | STOP | HOME | YES |
| B | 23分 | 5% | 60bpm | LV. 2 | 55bpm | LV. 1 | STOP | HOME | STOP | HOME | NO |
| ... | ... | ... | ... | ... | ... | ... | ... | ... | ... | ... | ... |

FIG. 10

MOBILE TERMINAL, RECOMMENDATION SYSTEM, AND RECOMMENDATION METHOD

RELATED APPLICATIONS

The present application claims the benefit of priority under 35 U.S.C. § 119 to Japanese Patent Application No. 2014-173480, which was filed on Aug. 28, 2014 and entitled, "Mobile Terminal, Recommendation Program, Recommendation System, and Recommendation Method," the contents of which are incorporated by reference herein in their entireties.

BACKGROUND OF THE DISCLOSURE

This disclosure relates to a mobile terminal, a recommendation system, and a recommendation method.

The use of a mobile terminal capable of playing music is widespread and users can listen to music at various locations. With the development of storage medium technology, large volumes of music data can be saved on the mobile terminal.

BRIEF DESCRIPTION OF THE DRAWINGS

FIG. 6 is an illustrative view illustrating an example of the configuration of a play log table stored in a RAM illustrated in FIG. 3.

FIG. 10 is an illustrative view illustrating another example of the configuration of the play log table stored in the RAM illustrated in FIG. 3.

DETAILED DESCRIPTION

First Embodiment

Figure 1:
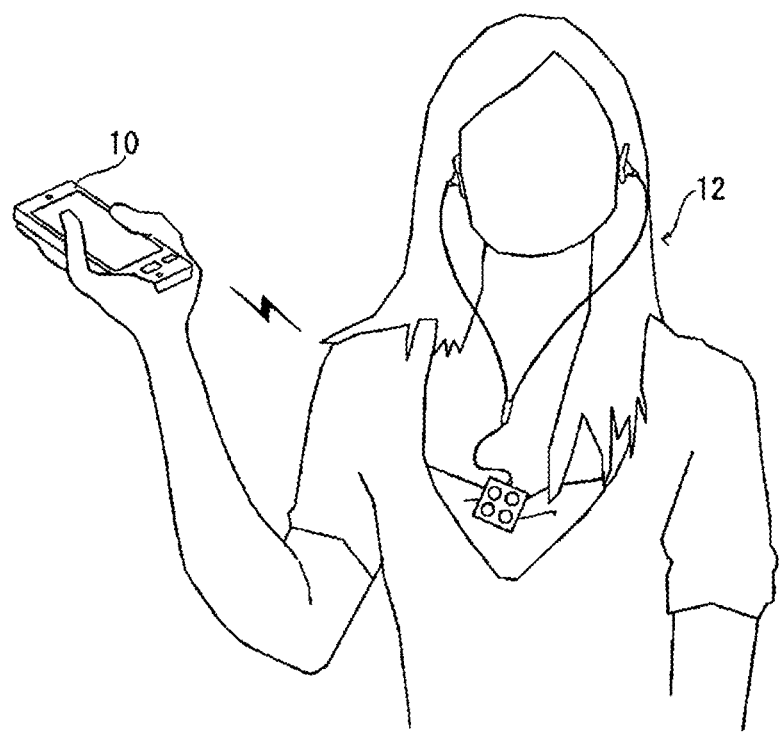
FIG. 1 is an illustrative view illustrating an example of a mobile phone of an embodiment of the present disclosure used with headphones.

With reference to FIG. 1, a mobile phone 10 of at least one embodiment is, for example, a smartphone, and is carried by a user. The user fits headphones 12 into his/her ears, and secures a housing 70 (refer to FIG. 4) of the headphones 12 onto his/her clothing. Then, the mobile phone 10 is wirelessly connected to the headphones 12 using Bluetooth (registered trademark) short-range wireless communication technology.

The mobile phone 10 has a music player function, and music is output from the wirelessly connected headphones 12 when an operation for playing music is performed on the mobile phone 10. While described in detail later, the headphones 12 can detect a heart rate of the user, and transmit the heart rate to the mobile phone 10.

This disclosure may be applied to any mobile terminal, such as a tablet terminal, a tablet PC, and a personal digital assistant (PDA).

Figure 2:
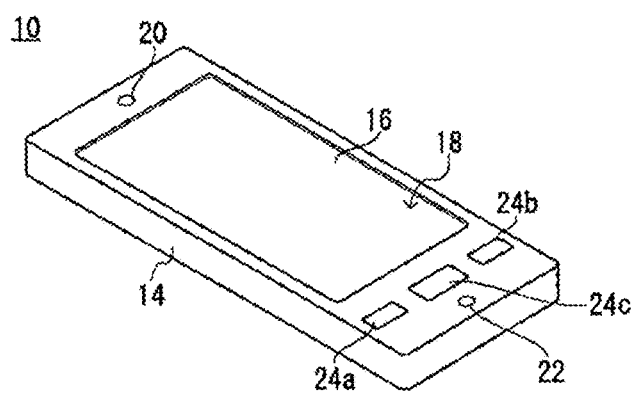
FIG. 2 is an external view illustrating an example of the outer appearance of the mobile phone illustrating in FIG. 1.

With reference to FIG. 2, the mobile phone 10 includes a housing 14 having a vertically long, flat rectangular shape. The main surface (surface) of the housing 14 is provided with a display 16 that is made of liquid crystal or organic EL, for example, and functions as a display unit. A touch panel 18 is provided on the display 16.

A speaker 20 is built into the main surface side of one end, and a microphone 22 is built into the main surface side of the other end in the vertical direction of the housing 14.

Along with the touch panel 18, hard keys 24 that constitute input operation means, including a call key 24a, an end call key 24b, and a menu key 24c in at least one embodiment, are provided on the main surface of the housing 14.

The user, for example, enters a telephone number by performing a touch operation on a dial pad displayed on the display 16. A voice call is then started when the user operates the call key 24a. The voice call is ended when the user operates the end call key 24b. The power of the mobile phone 10 can be turned ON and OFF by holding down the end call key 24b. Furthermore, the power of the display 16 and the touch panel 18 are turned OFF when the end call key 24b is pressed for a short time with a screen displayed on the display 16.

When the menu key 24c is operated, the home screen is displayed on the display 16. The user may then select an object by performing a touch operation via the touch panel 18 on a graphic user interface (GUI) displayed on the display 16 in this state, and applying the selection.

In the following description, the GUIs including icons, soft keys, and the like displayed on the display 16 are collectively referred to as objects.

Figure 3:
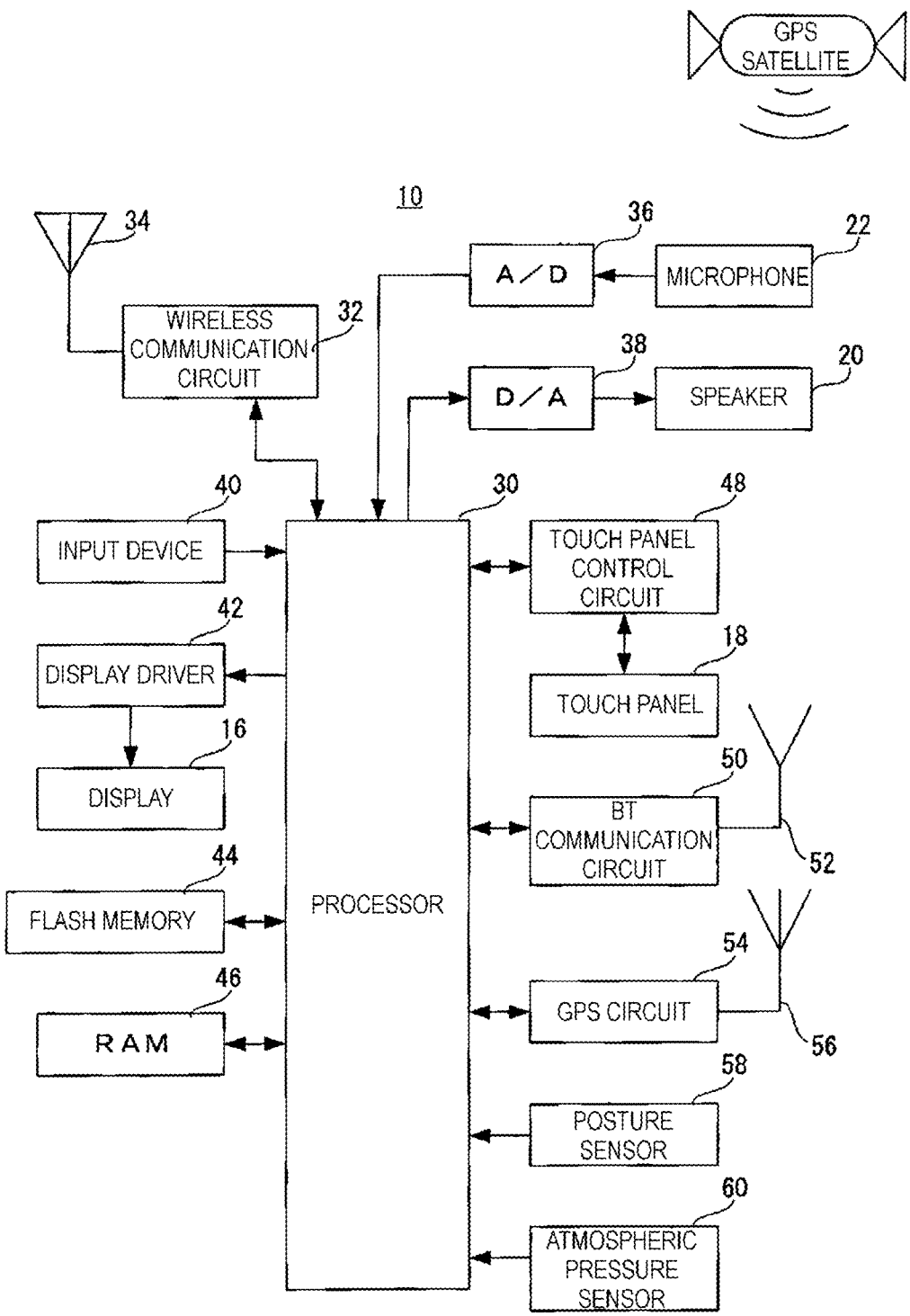
FIG. 3 is an illustrative view illustrating the electrical configuration of the mobile phone illustrated in FIG. 1.

With reference to FIG. 3, the mobile phone 10 of an embodiment illustrated in FIG. 2 includes a processor 30, also referred to as a computer or CPU, and the like. A wireless communication circuit 32, an analog-to-digital (A/D) converter 36, a digital-to-analog (D/A) converter 38, an input device 40, a display driver 42, a flash memory 44, a RAM 46, a touch panel control circuit 48, a Bluetooth (hereinafter abbreviated "BT") communication circuit 50, a global positioning system (GPS) circuit 54, a posture sensor 58, an atmospheric pressure sensor 60, and the like are connected to the processor 30. An antenna 34 is connected to the wireless communication circuit 32, the microphone 22 is connected to the A/D converter 36, the speaker 20 is connected to the D/A converter 38, the display 16 is connected to the display driver 42, the touch panel 18 is connected to the touch panel control circuit 48, a BT antenna 52 is connected to the BT communication circuit 50, and a GPS antenna 56 is connected to the GPS circuit 54.

The processor 30 is in charge of a whole control of the mobile phone 10. All or a part of a program set in advance in the flash memory 44 is, in use, expanded into the RAM 46 functioning as a storage unit, and the processor 30 operates in accordance with the program on the RAM 46. The RAM 46 is further used as a working area or buffer area for the processor 30. Then, a plurality of music content data is saved in the flash memory 44. Thus, the flash memory 44 is also sometimes called a saving unit.

The input device 40 includes the three hard keys 24 illustrated in FIG. 2. Thus, the input device 40 receives key operations performed on the hard keys 24. Information (key data) of the hard key 24 operated by the key operations is input to the processor 30 by the input device 40.

The wireless communication circuit 32 is a circuit for transmitting and receiving a radio wave for a voice call, email, or the like, via the antenna 34. According to at least one embodiment, the wireless communication circuit 32 is a circuit for performing a wireless communication with a code division multiple access (CDMA) system. For example, on the basis of an operation of an outgoing call (voice call) received by the touch panel 18, the wireless communication circuit 32, under instructions from the processor 30, executes voice call processing and outputs a voice call signal via the antenna 34. The voice call signal is transmitted to the other phone through a base station and a communication network. Then, when voice incoming processing is performed in the other phone, a communication-capable state is established and the processor 30 executes call processing. The wireless communication circuit 32 may be configured to be compatible with a communication system such as long-term evolution (LTE) system rather than the CDMA system.

The A/D converter 36 converts analog audio signals obtained from the microphone 22 as described above to digital audio data, and inputs the audio data to the processor 30. The D/A converter 38 converts digital audio data to analog audio signals, and applies the signals to the speaker 20 via an amplifier. Accordingly, audio based on audio data is output from the speaker 20. Then, with the call processing executed, the audio picked up by the microphone 22 is transmitted to the other phone, and the audio picked up by the other phone is output from the speaker 20. In a state in which music content is being played by the music player function, music is sometimes output from the speaker 20 as well.

The display 16 illustrated in FIG. 2 is connected to the display driver 42, and thus the display 16 displays a video or an image in accordance with video data or image data output from the processor 30. The display driver 42 includes video memory that temporarily stores data for display, and the data output from the processor 30 is stored in this video memory. Then, the display driver 42 displays an image on the display 16 in accordance with the content of the video memory. In other words, the display driver 42 controls a display by the display 16 connected to the display driver 42 under instructions from the processor 30. The display 16 is provided with a backlight, and the display driver 42 controls the brightness and on/off state of the backlight in accordance with instructions from the processor 30.

The touch panel 18 illustrated in FIG. 2 is connected to the touch panel control circuit 48. The touch panel control circuit 48 applies a necessary voltage or the like to the touch panel 18, and inputs a touch start signal indicating a start of a touch to the touch panel 18, a touch end signal indicating an end of a touch to the touch panel 18, and coordinate data indicating a touched touch position to the processor 30. The processor 30 then determines the touched object on the basis of this coordinate data and changes in the coordinate data.

For example, when the touch panel 18 is touched, a touch area is detected by the touch panel 18. The touch panel control circuit 48 at this time sets a centroid of the touch area as the touch position, and inputs the coordinates of the centroid to the processor 30. That is, the centroid of the touch area of the touch operation indicates a start touch position, an end touch position, or a current touch position. However, in at least one embodiment, the position initially touched on the touch panel 18 by a finger or the like may be considered the touch position rather than the centroid.

The touch panel 18 is a capacitive touch panel that detects a change in capacitance that occurs between the surface thereof and an object such as a finger (hereinafter referred to as "finger" as a matter of convenience). The touch panel 18 detects that one or more fingers touched the touch panel 18, for example. Accordingly, the user performs a touch operation on the surface of the touch panel 18, thereby inputting an operation position, operation direction, or the like to the mobile phone 10. Thus, the touch panel 18 is sometimes called a pointing device.

Here, the touch operations of at least one embodiment include a tap operation, long tap operation, flick operation, swipe (slide) operation, and the like.

The tap operation is performed by a user contacting (touching) the surface of the touch panel 18 with his/her finger and then releasing the finger from the surface of the touch panel 18 within a short time. The long tap operation is performed by a user contacting and holding his/her finger on the surface of the touch panel 18 and then releasing the finger from the surface of the touch panel 18. The flick operation is performed by a user contacting the surface of the touch panel with his/her finger and then flipping his/her finger at a predetermined velocity or greater in any direction. The swipe operation is performed by a user bringing his/her finger into contact with the surface of the touch panel 18, holding and moving the finger in any direction, and then releasing the finger from the surface of the touch panel 18.

The above described swipe operation also includes a swipe operation or so-called drag operation in which the user touches an object displayed on the surface of the display 16 with his/her finger and then moves the object. The operation in which the user releases his/her finger from the surface of the touch panel 18 after the drag operation is called a drop operation.

In the following description, the tap operation, long tap operation, flick operation, swipe operation, drag operation, and drop operation are each abbreviated as "operation." A touch operation is not limited to an operation by a finger of a user, and may be performed by a stylus pen or the like.

According to at least one embodiment, the power of the display 16 and the touch panel 18 is automatically turned OFF when a specific time (15 seconds, for example) has elapsed without an operation performed.

The BT communication circuit 50 establishes BT short-range wireless communication having a master and slave relationship between the headphones 12 and another communication device such as a headset.

For example, when the mobile phone 10 is set so that BT communication is enabled and the mobile phone 10 operates as the master, the mobile phone 10 searches for a communication device that operates as a slave. At this time, when the user performs an operation that executes BT wireless communication with the headphones 12, the headphones 12 of at least one embodiment operate as a slave and transition to a "connection standby state" for responding to a connection request from the master terminal. As a result, the mobile phone 10 that operates as the master can find the headphones 12 that operate as the slave. When the mobile phone 10 finds the headphones 12, the mobile phone 10 asks the user to enter a passcode (PIN) set for the headphones 12. If the mobile phone 10 receives input of the correct PIN, BT communication between the mobile phone 10 and the headphones 12 is established. Then, when BT communication is established, data reception and transmission can be performed. According to at least one embodiment, the data of music content or the like is transmitted from the mobile phone 10 to the headphones 12, and operation data for the music player function, data indicating a heart rate, and the like are transmitted from the headphones 12 to the mobile phone 10.

The GPS circuit 54 is activated when a current position is determined by the GPS function. When a GPS satellite signal received by the GPS antenna 56 is input, the GPS circuit 54 executes positioning processing on the basis of the GPS signal. As a result, the latitude, longitude, and elevation (altitude) are calculated as GPS information (position information).

While only one GPS satellite is drawn for simplicity in FIG. 1, GPS signals can be received from at least four GPS satellites for three-dimensional positioning of the current position. If GPS signals cannot be received from at least four GPS satellites, it is possible to calculate the longitude and latitude by two-dimensional positioning as long as GPS signals are received from three GPS satellites.

When the current position is determined by the GPS function, signals transmitted from a base station, signals transmitted from a wireless LAN access point, and the like may be utilized in addition to the GPS signals transmitted from the GPS satellites.

The posture sensor 58 detects the inclination and movement of the mobile phone 10. In the posture sensor 58, for example, a gyro sensor that detects the rotation (angular velocity) of the three axes (X, Y, and Z) of the mobile phone 10, and an acceleration sensor that detects acceleration in the three axial (X, Y, and Z) directions of the mobile phone 10 are integrally formed by micro electro mechanical systems (MEMS) technology. Thus, the posture sensor 58 is also sometimes called a six-axis motion sensor. Then, the processor 30 detects the inclination (angle) and movement of the mobile phone 10 on the basis of the angular velocities of the three axes and the accelerations in the three-axial directions output by the posture sensor 58.

For example, when any screen is displayed on the display 16, the processor 30 detects the posture in which the mobile phone 10 is held utilizing angular velocity and acceleration, and sets the display orientation in accordance with the detected posture. According to at least one embodiment, the display orientation is set to portrait if the mobile phone 10 is held in a vertical posture, and to landscape if the mobile phone 10 is held in a horizontal posture.

In at least one embodiment, the acceleration sensor and gyro sensor may each be provided in place of the posture sensor 58.

The atmospheric pressure sensor 60 is a semiconductor pressure sensor, and detects the ambient atmospheric pressure using an internally provided piezoresistive element. The processor 30 converts an output of the atmospheric pressure sensor 60 to an atmospheric pressure value, and calculates a pressure altitude (hereinafter, simply "altitude") in real-time on the basis of the atmospheric pressure value. For example, according to at least one embodiment, a slope of a road on which the user is moving and the like are estimated utilizing the calculated altitude. In at least one embodiment, a capacitive atmospheric pressure sensor formed by MEMS technology or the like may be used.

Furthermore, according to at least one embodiment, the movement of the user is detected utilizing the posture sensor 58 and the atmospheric pressure sensor 60. Thus, the posture sensor 58 and the atmospheric pressure sensor 60 are sometimes collectively referred to as a detecting unit.

Figure 4:
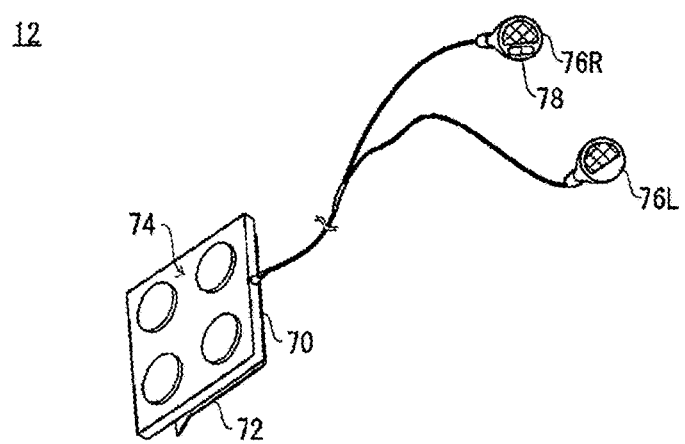
FIG. 4 is an external view illustrating an example of the outer appearance of the headphones illustrated in FIG. 1.

With reference to FIG. 4, the headphones 12 include the housing 70 having a flat, rectangular shape. A clip 72 for securing the housing 70 onto clothing or the like is provided on the back surface of the housing 70. An operation key group 74 for operating the headphones 12 is provided on the surface of the housing 70. A cable split into two midway is connected to a side surface of the housing 70. A right ear fitting unit 76R and a left ear fitting unit 76L are connected to each end of the cable. The two ear fitting units 76 have a so-called inner ear shape, and can be fit to the left and right ears of the user. A right speaker 84R (refer to FIG. 5) and a heart rate sensor 78 are provided to the right ear fitting unit 76R, and a left speaker 84L (refer to FIG. 5) is provided to the left ear fitting unit 76L.

The user, for example, secures the headphones 12 (housing 70) onto his/her clothing or the like utilizing the clip 72. The user operates each operation key included in the operation key group 74, turning ON/OFF the power of the headphones 12 and transitioning to a "connection standby state" of BT communication. With the mobile phone 10 and the headphones 12 performing BT communication, the user can play, stop, and select music and the like using the operation key group 74. The user can measure his/her own heart rate by the headphones 12 and check the measured heart rate using the mobile phone 10. Thus, the user can easily measure his/her own heart rate by wearing the headphones 12.

Figure 5:
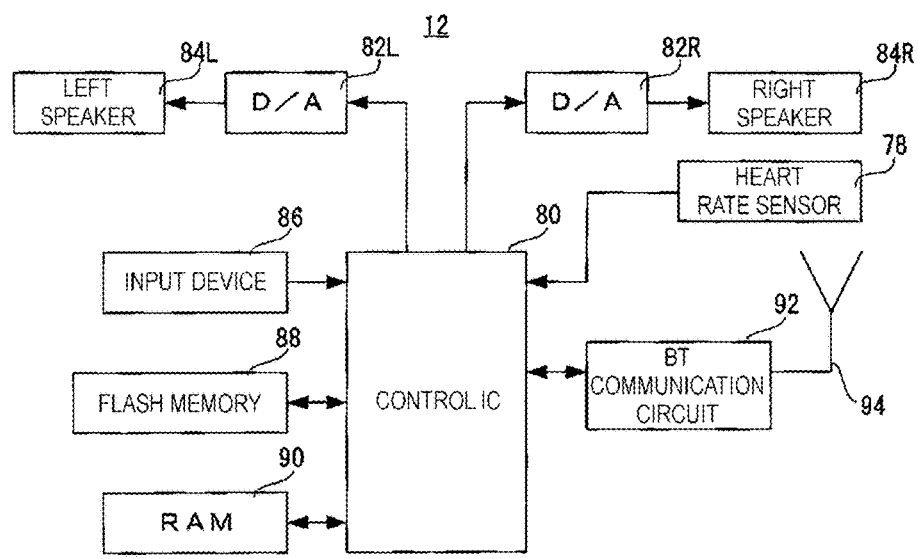
FIG. 5 is an illustrative view illustrating the electrical configuration of the headphones illustrated in FIG. 1.

With reference to FIG. 5, the headphones 12 of at least one embodiment illustrated in FIG. 1 include a control integrated circuit (IC) 80, also referred to as a computer or CPU, or the like. The heart rate sensor 78, a D/A converter 82L, a D/A converter 82R, an input device 86, a flash memory 88, a RAM 90, a BT communication circuit 92, and the like are connected to the control IC 80. The left speaker 84L is connected to the D/A converter 82L, the right speaker 84R is connected to the D/A converter 82R, and a BT antenna 94 is connected to the BT communication circuit 92.

The control IC is in charge of a whole control of the headphones 12. All or a part of a program set in advance in the flash memory 88 is, in use, expanded into the RAM 90, and the control IC 80 operates in accordance with the program on the RAM 90.

The input device 86 includes each operation key in the operation key group 74 illustrated in FIG. 4. Thus, when an operation key receives a key operation, the information of the operation key is input to the control IC 80 by the input device 86.

The D/A converter 82L and the D/A converter 82R convert the digital audio data received by the headphones 12 to analog audio signals, and provide the signals to the left speaker 84L and the right speaker 84R via the amplifier. If the audio data is stereo compliant, the control IC 80 outputs the audio data of corresponding channels to the D/A converter 82L and the D/A converter 82R. Accordingly, audio of different channels is output from the left speaker 84L and the right speaker 84R.

The BT communication circuit 92, similar to the BT communication circuit 50, establishes BT short-range wireless communication having a master and slave relationship with another communication device such as the mobile phone 10. For example, when an operation key is operated and BT communication is enabled, the BT communication circuit 92 operates as a slave, and transitions to a "connection standby state." Establishment of BT communication with the mobile phone 10 is described above, and therefore a detailed description thereof will be omitted.

The heart rate sensor 78 includes an LED that emits red light, and a phototransistor. When the heart rate sensor 78 operates, the LED emits red light on the surface of the ear where the headphones 12 are fitted, and a change in, i.e., the pulse of, the blood that passes through the blood vessels inside the ear is captured by the phototransistor. Further, according to at least one embodiment, the pulse rate per certain period of time measured in the ear of the user is transmitted to the mobile phone 10 as the heart rate of the user. The heart rate sensor 78 is also sometimes called a heart rate measuring unit.

According to the mobile phone 10, it is possible to calculate (output) physiological information, such as a stress level, for example, indicating the state of the user utilizing a plurality of heart rates (pulses) captured by the heart rate sensor 78. The stress level according to at least one embodiment indicates a balance between sympathetic and parasympathetic activities, and can serve as one index that indicates the state of the user. Then, according to at least one embodiment, the state of sympathetic and parasympathetic activities is found from a change in a timing at which a plurality of heart rates are captured, and the stress level is then calculated. The calculated stress levels are classified into five levels (LVs 1 to 5). For example, a stress level of LV 1 indicates the lowest stress level state, and a stress level of LV 5 indicates the highest stress level state.

Thus, according to at least one embodiment, the stress level indicating the state of the user can be calculated by utilizing physiological information such as a heart rate.

Because techniques for calculating a stress level on the basis of a heart rate are widely generally known, a detailed description thereof will be omitted. In at least one embodiment, the stress level may be calculated utilizing physiological information such as a state of perspiration of the user, a change in a pupil of the user, and brain waves of the user. Further, in at least one embodiment, the stress level may be output utilizing a table that associates heart rates and stress levels, or the like. For example, when a current heart rate is acquired, the stress level corresponding to the current heart rate is read from the above-described table.

The calculated stress level may be more finely classified. Rather than a stress level, a numerical value indicating a ratio of alpha waves or beta waves in brain waves, or the like may be utilized. In at least one embodiment, "stress level" is also sometimes called "level of relaxation" or the like. Then, according to at least one embodiment, the heart rate and stress level are collectively referred to as physiological information.

The mobile phone 10 according to at least one embodiment has a music player function as described above. Utilizing the music player function, the user can select any music content from a plurality of music contents stored in the flash memory 44 of the mobile phone 10, and listen to music. The user can optionally select the headphones 12 or the speaker 20 as the music output destination. Initial settings are configured so that music is output from the headphones 12 when music content is played. However, if the headphones 12 are not connected to the mobile phone 10, and the user performs a switch operation, the output destination switches to the speaker 20. Then, when the music player function of at least one embodiment is executed, music content matching the state of the user is displayed (recommended) on the display 16.

Here, in the first embodiment, a play log table (also called a database) that associates physiological information (stress levels) with music content is prepared in advance, and reference is made to the play log table on the basis of the calculated stress level. Then, music content that changes the stress level is selected by referring to the play log table, and the selected music content is recommended to the user.

FIG. 6 is an illustrative view illustrating an example of the configuration of the play log table. With reference to FIG. 6, the play log table includes a content column and a physiological information column, and the physiological information column further includes start heart rate and stress level columns, and end heart rate and stress level columns.

The content column stores information indicating the music content, such as the name of the music content. The start column stores the heart rate measured after the playing of the music content has started in the heart rate column, and the stress level (first stress level) calculated by measuring that heart rate in the stress level column. On the other hand, the end column stores the heart rate measured after the playing of the music content has ended in the heart rate column, and the stress level (second stress level) calculated by measuring that heart rate in the stress level column. Then, one row that includes these corresponds to one play log. According to this embodiment, a play log of music content is registered (added) each time music content is played. A play log is also sometimes called content information, or simply "information."

For example, when music content with the name "A" is played, the heart rate (80 bpm, for example) is measured and the stress level (LV 3, for example) is calculated when the playing of the music content has started. Further, the heart rate (140 bpm, for example) is measured and the stress level (LV 4, for example) is calculated once again when the playing ends. Then, a new play log (row) is registered in the play log table. The registered play log stores "A" in the content field, and "80 bpm" and "LV 3" as the heart rate and stress level when the music content was played, and "140 bpm" and "LV 4" as the heart rate and stress level when the playing of the music content ended.

Further, the states in which the playing of music content ends include the following: when the music content is played to the end, when the user performs an operation that stops the playing, when the user selects other music content (makes a song selection), when the music player function is exited, and when wireless communication with the headphones is interrupted. That is, when music content is playing, the playing of the music content is assessed as having ended when any one of the above states has occurred. However, if the headphones 12 have a wired connection, the playing of the music content ends also when a plug of the headphones 12 is removed from the mobile phone 10.

Furthermore, according to the first embodiment, if a play time of music content is less than a predetermined time (2 seconds, for example), the play log is not registered in the play log table. The reason is that, when other music content has been selected by a song feed immediately after the music content was played, the music content before the song selection cannot be considered as having been substantially played.

Next, when the music player function is executed, the current stress level is calculated and whether or not that stress level is greater than a predetermined value (LV 3, for example) is assessed. Then, if the current stress level is greater than the predetermined value, music content having a high potential to decrease the stress level is selected. Here, music content having a high potential to decrease the stress level refers to music content indicated by a play log having a lower end stress level than a start stress level in the play log table.

For example, in the play log table shown in FIG. 6, the music content "A" has a greater end stress level (LV 4) than a start stress level (LV 3). In contrast, for example, the music content "B" has a lower end stress level (LV 1) than a start stress level (LV 2). As a result, music content "B" is selected and recommended to the user. According to this embodiment, when content is recommended, information indicating the selected content and the like are displayed on the display 16. In this manner, if the stress level of the user is high, it is possible to recommend music content that can be expected to have a stress level decreasing effect.

As understood from the above description, according to this embodiment, it is possible to determine the state of the user from physiological information and recommend music content suitable to the state of the user at that time.

Further, according to this embodiment, music content is recommended when the music player function is executed, that is, before music content is played. Thus, the user can refer to the recommended music content when selecting the music content to be played.

Further, when the user has selected and played recommended music content, the play log at that time is newly registered in the play log table. That is, because the play log table is updated every time optionally selected music content (hereinafter "optional content") is played by the user, it is possible to reflect preferences of the user in the play log table. As a result, the recommended music content more readily aligns with the preferences of the user.

If there are two or more music contents having a high potential to decrease the stress level, the two or more music contents may be simultaneously recommended. Further, if two or more music contents are displayed (recommended) in a tiled view, the contents may be tiled in descending order on the basis of the difference between the two stress levels, or randomly tiled.

Further, if the current stress level is less than a predetermined value, music content with a high play frequency is selected and recommended. In this case, the music content with a high play frequency can be selected by referring to the play log table that registers play logs. Thus, even if the stress level of the user is low, it is possible to recommend music content having a high user listening potential to the user.

When music content having a high play frequency is recommended, two or more music contents may be recommended, tiling the music contents in descending play frequency order. Further, even when physiological information cannot be acquired, that is, even if the heart rate of the user cannot be measured, music content having a high play frequency is recommended to the user.

While music content is recommended so as to decrease a stress level according to the first embodiment, music content may be recommended so as to increase a stress level in other embodiments.

The above has outlined the special characteristics of the first embodiment. The following describes the details thereof using the memory map illustrated in FIG. 7 and the flowcharts illustrated in FIG. 8 and FIG. 9.

Figure 7:
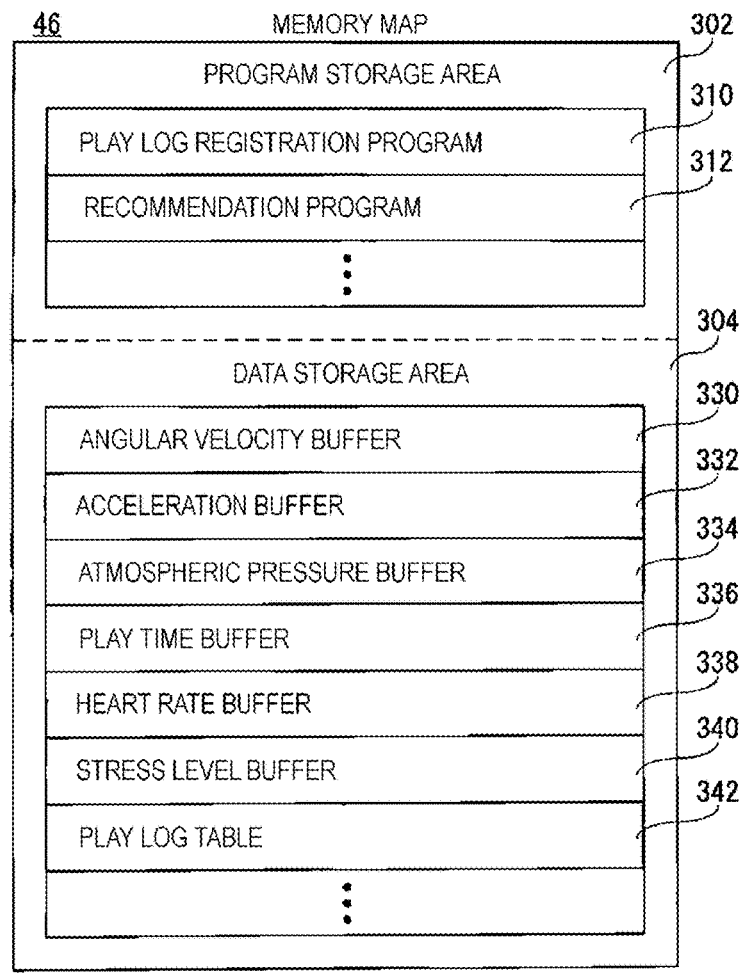
FIG. 7 is an illustrative view illustrating an example of a memory map of the RAM of the mobile phone illustrated in FIG. 3.

With reference to FIG. 7, a program storage area 302 and a data storage area 304 are formed in the RAM 46. The program storage area 302, as described above, is an area for storing (expanding) a part or whole of the program data set in advance in the flash memory 44 (FIG. 2) by reading the same.

The program storage area 302 stores a play log registration program 310 for registering a play log when music content has been played in a play log table, a recommendation program 312 for recommending music content, and the like. The program storage area 302 also stores programs for executing the music player function and the like.

Then, the data storage area 304 of the RAM 46 is provided with an angular velocity buffer 330, an acceleration buffer 332, and atmospheric pressure buffer 334, a play time buffer 336, a heart rate buffer 338, a stress level buffer 340, and the like. The data storage area 304 stores a play log table 342 and the like.

The angular velocity buffer 330 temporarily stores each of the angular velocities of the three axes output from the posture sensor 58. The acceleration buffer 332 temporarily stores each of the accelerations of the three axes output from the posture sensor 58. The atmospheric pressure buffer 334 temporarily stores the ambient atmospheric pressure detected by the atmospheric pressure sensor 60. The play time buffer 336 temporarily stores the play time of the music content being played. The heart rate buffer 338 temporarily stores the heart rate measured by the heart rate sensor 78 and received from the headphones 12. The stress level buffer 340 temporarily stores the calculated stress level.

The play log table 342 is a table having the configuration illustrated in FIG. 6, for example, and includes a plurality of play logs.

The data storage area 304 stores address book data and the like, and provides other flags and timers (counters) necessary for program execution.

Figure 8:
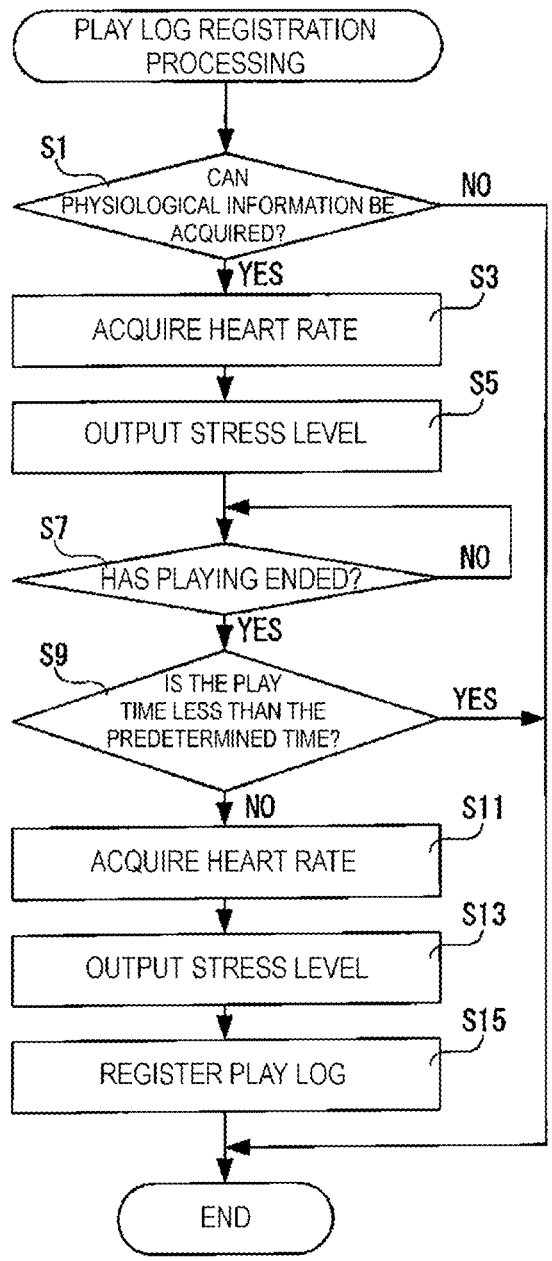
FIG. 8 is a flowchart illustrating an example of the play log registration processing of the processor illustrated in FIG. 3.
Figure 9:
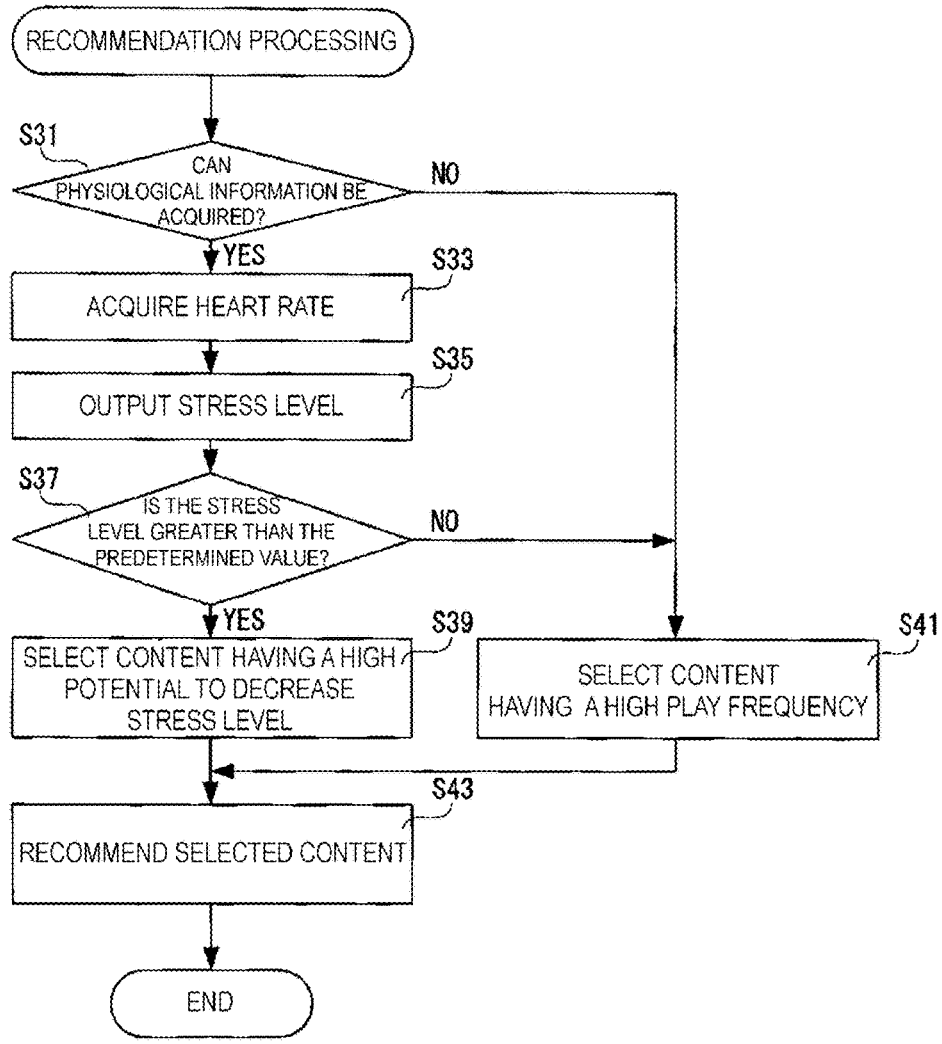
FIG. 9 is a flowchart illustrating an example of the recommendation processing of the processor illustrated in FIG. 3.

The processor 30 processes a plurality of tasks including play log registration processing illustrated in FIG. 8, recommendation processing illustrated in FIG. 9, and the like in parallel, under controls by a Windows (registered trademark) based OS, a Linux (registered trademark) based OS such as Android (registered trademark) and iOS (registered trademark), or other OSs.

FIG. 8 is a flowchart of the play log registration processing. For example, when music content is played by the music player function, the play log registration processing is started. When the play log registration processing is executed, the mobile phone 10 issues a command to the headphones 12 to transmit data indicating the heart rate. The headphones 12 measure the heart rate in accordance with the command, and transmit the heart rate to the mobile phone 10.

In step S1, the processor 30 determines whether or not physiological information can be acquired. That is, the processor 30 determines whether or not the heart rate of the user has been measured and stored in the heart rate buffer 338. If the determination is "No" in step S1, that is, if the right ear fitting unit 76R has not been fitted to the ear of the user and the heart rate cannot be measured, for example, the processor 30 ends the play log registration processing.

On the other hand, if "Yes" is determined in step S1, that is, if a measured heart rate has been stored in the heart rate buffer 338, the processor 30 acquires the heart rate in step S3. In other words, the processor 30 reads the measured heart rate from the heart rate buffer 338. Then, in step S5, the processor 30 outputs a stress level. That is, the processor 30 outputs a stress level on the basis of the read heart rate. Further, the calculated stress level is stored in the stress level buffer 340 as the first stress level.

Then, in step S7, the processor 30 determines whether or not playing has ended. In other words, the processor 30 determines if the playing of the music content has ended. If "No" is determined in step S7, that is, if the playing of the music content has not ended, the processor 30 repeats the processing of step S7. On the other hand, if "Yes" is determined in step S7, that is, if the music content has played to the end, for example, the processor 30 determines whether or not the play time was less than a predetermined time in step S9. That is, the processor 30 determines if the play time of the music content stored in the play time buffer 336 is less than the predetermined time (2 seconds, for examples). If "Yes" is determined in step S9, that is, if a song feed operation is performed immediately after the music content was played and the play time was less than the predetermined time, for example, the processor 30 ends the play log registration processing. That is, the play log is not registered in the play log table 342.

On the other hand, if "No" is determined in step S9, that is, if the play time of the music content is greater than the predetermined time, the processor 30 acquires a heart rate in step S11 and outputs a stress level in step S13. In other words, because the playing of the music content has ended, the processor 30 acquires an end heart rate and calculates the second stress level.

Then, in step S15, the processor 30 registers a play log. That is, a play log is created on the basis of the heart rate and stress level when the playing of the music content was started, the heart rate and stress level when the playing was ended, and the name of the played music content, and the play log is registered in the play log table 342. Then, when the processing of step S15 ends, the processor 30 ends the play log registration processing. The processor 30 that executes the processing of step S15 functions as a registering unit.

Further, in other embodiments, the processing of step S9 in the play log registration processing, that is, the processing for determining whether or not the play time is greater than the predetermined time, may be omitted.

FIG. 9 is a flowchart of the recommendation processing. For example, when the music player function is executed, the recommendation processing is started. When the recommendation processing is executed as well, a command to transmit data indicating the heart rate is output to the headphones 12.

In step S31, similar to step S1, the processor 30 determines whether or not physiological information can be acquired. If "No" is determined in step S31, that is, if the heart rate has not been measured, for example, the processor 30 proceeds to the processing of step S41. On the other hand, if "Yes" is determined in step S31, that is, if the heart rate has been measured, for example, the processor 30 acquires the heart rate in step S33 and outputs the stress level in step S35 in the same manner as steps S3 and S5.

Then, in step S37, the processor 30 determines whether or not the stress level is greater than a predetermined value. For example, the processor 30 determines whether or not the current stress level stored in the stress level buffer 340 is greater than a predetermined value (LV 3, for example). If "Yes" is determined in step S37, that is, if the current stress level is LV 4 and greater than the predetermined value, for example, the processor 30 selects content having a high potential to decrease the stress level in step S39. That is, the processor 30 refers to the play log table 342 and selects music content indicated by a play log having a second stress level that is less than a first stress level from a plurality of music content stored in the flash memory 44. Once the processing of step S39 ends, the processor 30 proceeds to the processing of step S43. The processor 30 that executes the processing of step S39 functions as a selecting unit.

On the other hand, if "No" is determined in step S37, that is, if the current stress level is LV 2 and less than the predetermined value, for example, the processor 30 selects content having a high play frequency in step S41. That is, the processor 30 refers to the play log table 342 and selects music content having a high play frequency. Once the processing of step S41 ends, the processor 30 proceeds to the processing of step S43. The processor 30 that executes the processing of step S41 functions as a play frequency selecting unit.

Then, in step S43, the processor 30 recommends the selected content. For example, if music content "B" is selected on the basis of the play log table illustrated in FIG. 6, the music content "B" is displayed (recommended) on the display 16. Further, if the music content "A" is selected as music content having a high play frequency, the music content "A" is displayed on the display 16. Then, when the processing of step S43 ends, the processor 30 ends the recommendation processing.

The processor 30 that executes the processing of steps S39, S41, and S43 functions as a recommending unit. Further, the processor 30 that executes the processing of steps S3 and S11 of the play log registration processing and step S33 of the recommendation processing functions as an acquiring unit. Further, the processor 30 that executes the processing of steps S5 and S13 of the play log registration processing and step S35 of the recommendation processing functions as an output unit.

Second Embodiment

According to the second embodiment, music content suited to the state of the user is recommended by further utilizing behavioral information that indicates the behavior of the user is in addition to physiological information. The outer appearance, the electrical configuration, and the like of the mobile phone 10 and the headphones 12 are substantially the same as the first embodiment, and detailed descriptions thereof will be omitted.

FIG. 10 is an illustrative view illustrating an example of the configuration of the play log table of the second embodiment. With reference to FIG. 10, according to the play log table of the second embodiment, fields including total play time, play percentage, and behavioral information are added to the play log table of the first embodiment. The content field and physiological information field (the same as each field included in the physiological information field) are the same as the first embodiment.

In the play log table of the second embodiment, the total play time field stores all time periods when the corresponding music content was played. The play percentage field stores the percentage (%) of actual play time to the total play time of the music content.

The behavioral information field includes a start operation mode field and play location field, an end operation mode field and play location field, and a song selection field. The start operation mode field stores the operation mode when the playing of the music content is started, and the end operation mode field stores the operation mode when the playing of the music content has ended. Similarly, the start play location field stores the location where the music content was played, and the end play location field stores the location where the playing of the music content was ended. Further, the song selection field stores data (Yes/No) indicating if a song selection operation has been performed when music content is being played.

The operation mode refers to the behavior of the user, and is determined on the basis of the output of the posture sensor 58 and the atmospheric pressure sensor 60. For example, if the user is walking, it is possible to assess the user as walking from a change in acceleration output by the posture sensor 58, and thus the operation mode is set to "Walk." Similarly, if the user is running, the user is assessed as running from a change in acceleration, and thus the operation mode is set to "Run." If the acceleration and angular velocity values output by the posture sensor 58 are less than threshold values, the user is assessed as stopped, and the operation mode is set to "Stop." If the altitude changes on the basis of the output of the atmospheric pressure sensor 60 and the acceleration changes, the user most likely is going up a hill, stairs, or the like, and thus the operation mode is set to "Climb." In other embodiments, the user may be detected as occupying a train, vehicle, or the like by combining the play location and a change in acceleration, and the operation mode at that time may be set to "In a vehicle." In this manner, according to the second embodiment, the behavioral information of the user can be acquired by utilizing a change in acceleration. Further, in other embodiments, the behavioral information of the user may include just the operation mode. Furthermore, the operation mode may be determined by utilizing just the acceleration output by the posture sensor 58.

The location stored in the location field is determined on the basis of a position determined by the GPS function. Specifically, "Home," "Park," and the like are registered in advance (bookmarked) in the mobile phone 10. Then, when music content is played, the current position is determined and the area in which the current position is included is set as the play location. While "Home" and the like are registered by the user in advance, "Park" and the like may be registered in default settings. Further, the play location may be specified in combination with map data. For example, if the current position is on a rail line and the acceleration is changing, the play position is set to "Train." Further, if an amount of change in acceleration is significant and the current position is not on a rail line, the play position is set to "Car."

For example, if the user had listened to music "A" when training in a park, the play log of music content "A" is registered in the play log table illustrated in FIG. 10. This play log indicates that the play time for the music content "A" is "10 minutes" and that the user played the music to the end (play percentage: 100%) without selecting a song (No) in the "Park." Further, the music content "A" was played when the user was walking ("Walk"), the heart rate at the time was "80 bpm," and the stress level was "LV 3." Further, the play log indicates that, after the playing of the music content "A" ended, the user was running ("Run"), the heart rate at that time was "140 bmp," and the stress level was "LV 4."

According to the second embodiment, the fact that songs were fed during the playing of the music content is stored, and thus a play log is registered even if the period of time the music content was actually played is less than a predetermined time.

Next, when the music player function is executed, the pulse rate of the user is acquired, the current stress level is calculated (output), and the behavioral information indicating the behavior of the user is acquired. Reference is made to the play log table on the basis of the stress level and behavioral information of the user, and a search is conducted for music content similar to the current state of the user. Then, when music content is found by the search, the music content is recommended.

The following specifically describes the search. According to the second embodiment, a search is conducted in the play log table for music content having associated physiological information and behavioral information similar to the current physiological information and behavioral information of the user. "Collaborative filtering" which is a type of recommendation algorithm, is utilized to search for such music content.

When collaborative filtering is utilized, it is possible to search for the state of the user when he/she had listened to the music content in the past, referring to the play log table based on the current state of the user. Specifically, the degree of similarity of the physiological information and behavioral information included in each play log to the current physiological information and behavioral information of the user is calculated. In other words, the degree of similarity to each play log is calculated. Then, the play log having a degree of similarity that is the highest and greater than a fixed value (70%, for example) becomes the search results based on collaborative filtering. Further, when the play log is acquired as the search results, the music content indicated by the play log is recommended to the user.

By thus utilizing collaborative filtering, it is possible to search the play log table for a past state of the user that is similar to the current state of the user. Then, music content indicated by the past state (play log) of the user found by the search, that is, the music content listened to by the user in the past in a state similar to the current state, can be recommended to the user.

For example, when the user is about to listen to music before going to sleep at home, the music content that he/she listened to before going to sleep previously (such as music content "B," for example) is recommended. Further, when the user is about to listen to music when training, the music content that he/she listened to when training previously (such as music content "A," for example) is recommended.

By thus utilizing the behavioral information of the user, it is possible to recommend more suitable music content in line with the state of the user.

Further, if music content had been played in a state in which physiological information cannot be acquired, a play log that does not include physiological information is registered. Further, if the music player function was executed in a state in which physiological information cannot be acquired, a search for music content is conducted without utilizing the physiological information. That is, even if physiological information cannot be acquired, it is possible to recommend music content by utilizing the behavioral information of the user. Thus, in a search based on collaborative filtering, the search may be conducting utilizing just a part and not all of the information included in the play log.

In other embodiments, the recommended music content may be a predetermined quantity (three, for example) recommended in descending order based on the level of similarity, rather than just the music content having the highest level of similarity. Further, in other embodiments, a "content-based" recommendation algorithm that utilizes played music content may be adopted with music content being played.

Further, in yet other embodiments, a "rule-based" recommendation algorithm that determines the music content to be recommended from current physiological information and behavioral information, or the like may be adopted as the recommendation algorithm.

Further, the play log of other embodiments may include information (the headphones 12 or the speaker 20) indicating the output destination of the music.

Further, when music content is recommended when the user is training, the music content may be selected on the basis of the heart rate corresponding to the exercise intensity when the training is performed. For example, when training is managed so that the heart rate becomes 120 bpm, music content having a tempo (BPM) of 120 may be recommended.

The above has outlined the special characteristics of the second embodiment. The following describes the details using the memory map illustrated in FIG. 11 and the flowcharts illustrated in FIG. 12 and FIG. 13.

Figure 11:
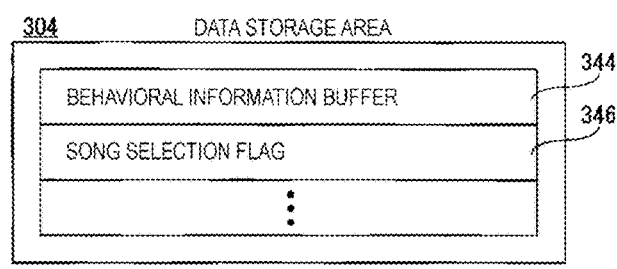
FIG. 11 is an illustrative view illustrating another example of the data storage area of the RAM of the mobile phone illustrated in FIG. 3.

With reference to FIG. 11, the data storage area 304 of the second embodiment is further provided with a behavioral information buffer 344 and a song selection flag 346 in addition to the buffers, data, and the like of the first embodiment.

The behavioral information buffer 344 stores the behavior mode and the like determined on the basis of the play position, which is determined on the basis of the current position determined by the GPS function, and the output of the posture sensor 58 and the atmospheric pressure sensor 60.

The song selection flag 346 is a flag that indicates that a song selection operation has been performed. For example, the song selection flag 346 is configured by a 1-bit register. When the song selection flag 346 is turned ON (is established), the data value "1" is set in the register. On the other hand, when the song selection flag 346 is turned OFF (is not established), the data value "0" is set in the register.

Figure 12:
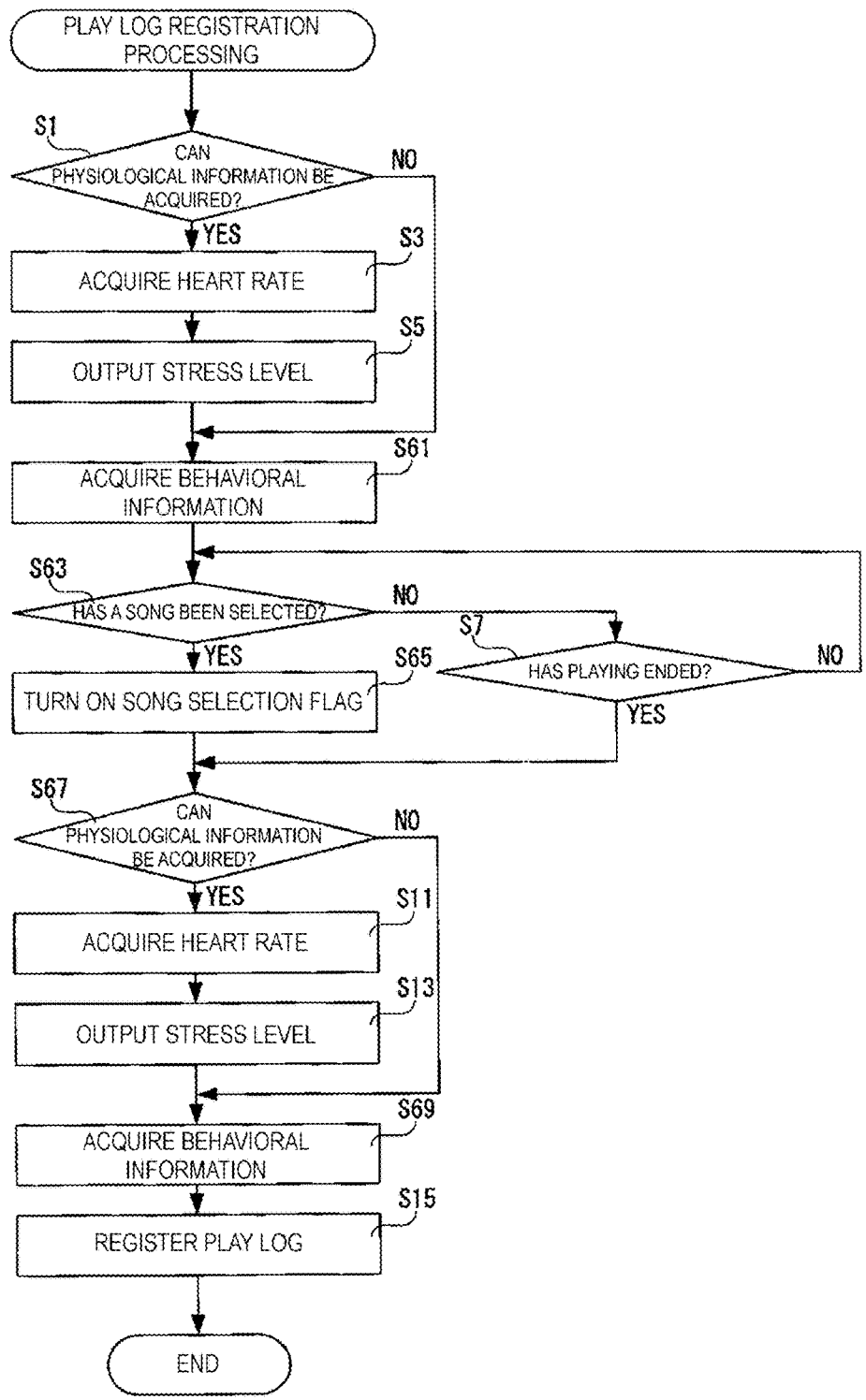
FIG. 12 is a flowchart illustrating another example of the play log registration processing of the processor illustrated in FIG. 3.

FIG. 12 is a flowchart of the play log registration processing of the second embodiment. The processing is substantially equivalent to that executed in the play log registration processing of the first embodiment, and a detailed description thereof will be omitted.

In step S1, the processor 30 determines whether or not physiological information can be acquired. If "No" is determined in step S1, that is, if physiological information cannot be acquired, the processor 30 proceeds to the processing of step S61. On the other hand, if "Yes" is determined in step S1, the processor 30 acquires the heart rate in step S3 and outputs the stress level in step S5.

Then, in step S61, the processor 30 acquires the behavioral information. The processor 30 acquires the operation mode and play location when the playing of the music content was started. Specifically, the processor 30 determines the operation mode on the basis of the output of the posture sensor 58 and the atmospheric pressure sensor 60, and determines the play location on the basis of the current position acquired by the GPS function. Then, the operation mode and play location are stored in the behavioral information buffer 344.

Then, in step S63, the processor 30 determines whether or not a song has been selected. That is, the processor 30 determines if a song selection operation has been performed when music content is being played. If "No" is determined in step S63, that is, if a song selection operation has not been performed, the processor 30 determines whether or not playing has ended in step S7. If "Yes" is determined in step S7, that is, if the playing of the music content has ended, the processor 30 proceeds to the processing of step S67. On the other hand, if "No" is determined in step S7, the processor 30 returns to the processing of step S63. Then, if "Yes" is determined in step S63, that is, if a song selection operation is performed, the processor 30 turns ON the song selection flag 346 in step S65.

Then, in step S67, similar to step S1, the processor 30 determines whether or not physiological information can be acquired. If "No" is determined in step S67, that is, if physiological information cannot be acquired, the processor 30 proceeds to the processing of step S69. On the other hand, if "Yes" is determined in step S67, the processor 30 acquires the heart rate in step S11 and outputs the stress level in step S13.

Then, in step S69, the processor 30 acquires the operation mode and the play location when the playing of the music content has ended. Then, the acquired operation mode and play location are stored in the behavioral information buffer 344. The specific processing is the same as step S61, and a detailed description thereof will be omitted.

Then, in step S15, the processor 30 registers a play log. That is, the processor 30 reads the information indicating the played music content and the total play time, calculates the play percentage on the basis of the play time read from the play time buffer 336, reads the heart rate and stress level from the heart rate buffer 338 and the stress level buffer 340, reads the operation mode and play location from the behavioral information buffer 344, and creates a play log. Further, the processor 30 determines the content of the song selection field on the basis of the state of the song selection flag 346. Then, the processor 30 registers (adds) the play log thus created to the play log table 342. Then, when the processing of step S15 ends, the processor 30 ends the play log registration processing. Furthermore, when the play log registration processing ends, the processor 30 initializes (turns OFF) the song selection flag 346.

Figure 13:
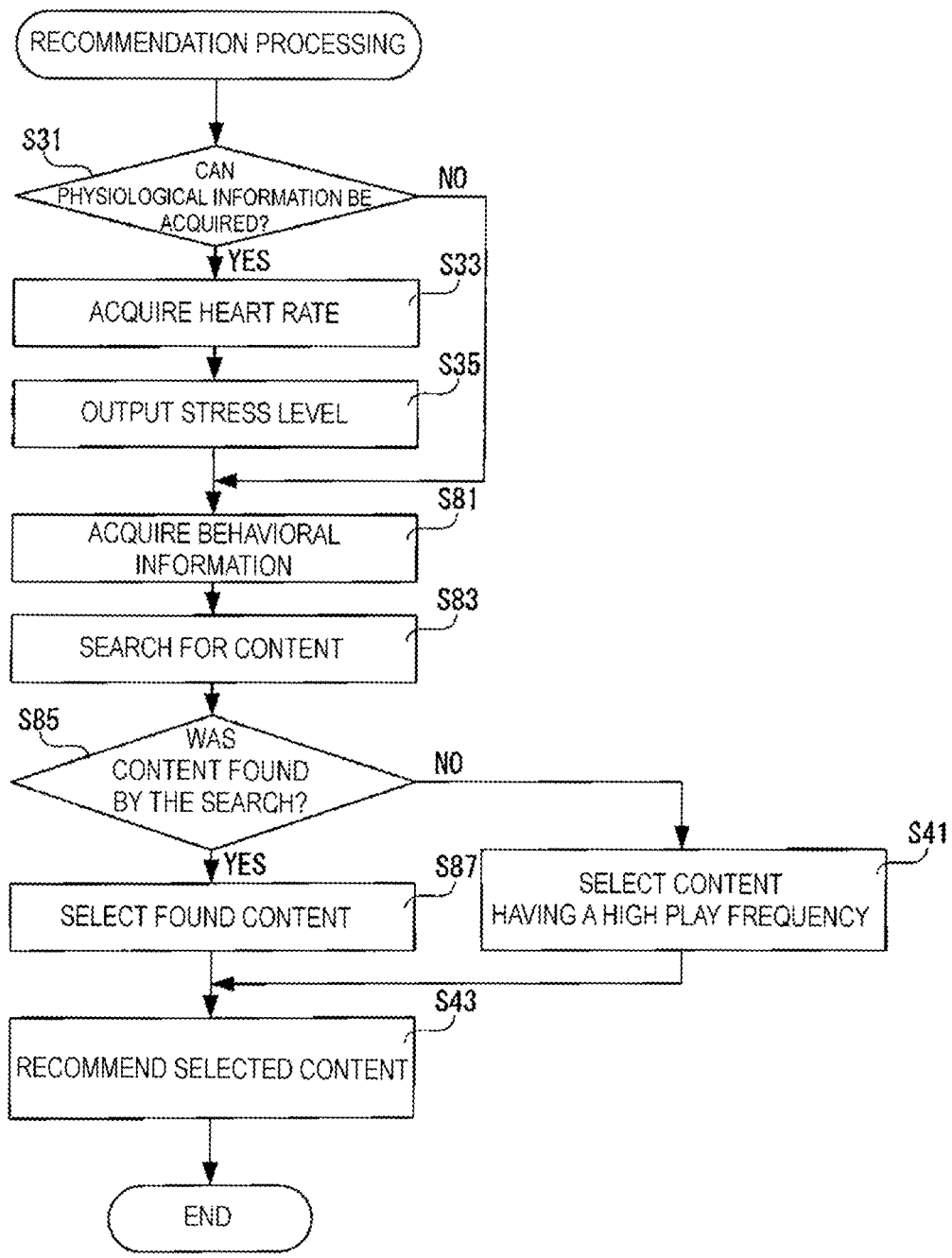
FIG. 13 is a flowchart illustrating another example of the recommendation processing of the processor illustrated in FIG. 3.

FIG. 13 is a flowchart of the recommendation processing of the second embodiment. The processing is substantially equivalent to that executed in the recommendation processing of the first embodiment, and a detailed description thereof will be omitted.

In step S31, the processor 30 determines whether or not physiological information can be acquired. If "No" is determined in step S31, that is, if physiological information cannot be acquired, the processor 30 proceeds to the processing of step S81. On the other hand, if "Yes" is determined in step S31, the processor 30 acquires the heart rate in step S33 and outputs the stress level in step S35.

Then, in step S81, the processor 30 acquires the behavioral information. That is, the current behavioral information is determined on the basis of the output of the posture sensor 58 and the atmospheric pressure sensor 60. Further, although before the music content is played, the play location is determined from the current position of the user. Then, the current operation mode and play location are stored in the behavioral information buffer 344.

Then, in step S83, the processor 30 searches for content. For example, the processor 30 searches for music content to recommend utilizing the aforementioned "collaborative filtering" recommendation algorithm. The processor 30 that executes the processing in step S83 functions as a searching unit.

Then, in step S85, the processor 30 determines whether or not content has been found by the search. For example, the processor 30 determines if a play log indicating a past state of the user that is similar to the current behavior of the user has been found by the search. If "Yes" is determined in step S85, that is, if a play log has been found by the search, the processor 30 selects the found content in step S87. That is, the music content corresponding to the found play log is selected. Then, when the processing of step S87 ends, the processor 30 proceeds to the processing of step S43. On the other hand, if "No" is determined in step S85, that is, if a play log could not be found by the search, the processor 30 selects content having a high play frequency in step S41. Then, when the processing of step S41 ends, the processor 30 proceeds to the processing of step S43.

Then, in step S43, the processor 30 recommends the selected content. For example, when the user is about to listen to music before going to sleep at home, the music content "B" indicated in the play log table illustrated in FIG. 10 is selected in the processing of step S87. Then, information indicating the selected music content "B" is displayed (recommended) on the display 16. Then, when the processing of step S43 ends, the processor 30 ends the recommendation processing.

In the second embodiment, the processor 30 that executes the steps S41, S43, and S87 functions as a recommending unit. Further, the processor 30 that executes the steps S61 and S69 of the play log registration processing of the second embodiment or step S81 of the recommendation processing of the second embodiment functions as a behavioral information acquiring unit.

Further, the first embodiment and the second embodiment can be optionally combined and, because specific combinations are easily imaginable, detailed descriptions thereof will be omitted.

Further, while the music content of this embodiment had been saved in the flash memory 44, the music content may be saved in an external recording medium, another terminal, a server, or the like. Further, if the music content of another terminal or a server has been played, an ID for identifying the other terminal, the URL for specifying the server, or the like is also stored in the play log. Further, the music content data saved in the other terminal or server may be moved to the flash memory 44 of the mobile phone 10 by data communication or the like.

Further, the play log tables of a plurality of mobile phones 10 may be collected on a server or the like, and one play log table that includes the play logs of various users may be created. Then, such the play log table may be distributed to the mobile phone 10 from a server or the like. Accordingly, it is possible to suitably recommend music content to even a user having a small play count of music content.

Further, the processing for selecting recommended music content may be executed on a system that includes a computer (device or server) on a network rather than the mobile phone 10. In this case, the physiological information and behavioral information acquired by the mobile phone 10 is transmitted to the system, and the data of the music content or the information indicating the music content selected by the system is transmitted to the mobile phone 10.

When the music content is recommended, not only may the information of the recommended music content be displayed on the display 16, but audio indicating the information of the music content may be output from the speaker 20 as well.

Further, the play logs included in the play log table may further include date and time information indicating when the playing of the music content was started, a play count of the music content, and the like. Further, if surrounding weather information can be acquired from a network or the like, weather information such as the weather and ambient temperature when the music content had been played may be included in the play log as well.

Further, while the playing of music content has been described in at least one embodiment, moving image content, book content, or the like may be recommended in at least one embodiment when the user views moving image content, browses book content, or the like, in the same manner as when the user listens to music.

Further, in at least one embodiment, a headset with a microphone added to the headphones 12 or the like may be utilized. Further, the mobile phone 10 and the headphones 12 may have a wired connection. Further, the headphones 12 are also sometimes called earphones. Further, while the ear fitting unit 76 of the headphones 12 of at least one embodiment is a so-called inner ear type, the ear fitting unit 76 may be a canal type or a head-mount type in at least one embodiment.

Further, in at least one embodiment, the heart rate sensor 78 may be fitted to a wristwatch type wearable terminal or the like rather than the headphones 12, and worn on an arm of the user. In this case, the mobile phone 10 may be included in the wearable terminal. In this case, earphones are connected to the wearable terminal.

Further, in at least one embodiment, the heart rate sensor 78 that directly measures the heart rate may be utilized. In this case, a chest belt that includes this heart rate sensor 78 is worn by the user. Further, the heart rate sensor 78 utilized may be a sensor provided with an LED that emits green light. Furthermore, the heart rate sensor 78 utilized may be an MEMS device that detects vibration near a blood vessel, or a sensor that detects a change in the movement (pulse) of a blood vessel by a captured moving image.

Further, in at least one embodiment, the recommended music content may be automatically played without relation to an operation by the user, even if music content has been recommended and there is no operation by the user.

Further, while words such as "greater than" have been used in relation to threshold values (predetermined values and the like) in the aforementioned embodiments, "greater than a threshold value" includes the meaning "greater than or equal to a threshold value." Further, "less than a threshold value" includes the meaning "less than or equal to a threshold value" as well as "less than a threshold value."

Further, the program used in at least one embodiment may be stored on an HDD of a server for data distribution, and distributed the mobile phone 10 via a network. With a plurality of programs stored on a storage medium such as an optical disk, including a CD, DVD, or Blue-ray disk (BD), or the like, USB memory, a memory card, or the like, the storage medium may be sold or distributed. Then, when a program is downloaded via the above described server, storage medium, or the like and installed on a mobile phone having the same configuration as at least one embodiment, the same advantages as at least one embodiment can be achieved.

The specific numerical values given in this description are merely examples, and may be suitably changed in accordance with product specification changes and the like.

What is claimed is:

1. A mobile terminal, comprising:
    at least one sensor that acquires physiological information, wherein the physiological information comprises a pulse rate of a user of the mobile terminal;
    a memory that stores a plurality of audio contents and a database that associates stress level information with each of the plurality of audio contents; and
    at least one processor configured to, when physiological information has been acquired by the at least one sensor, refers to the database and recommends a specific audio content from the plurality of audio contents, on the basis of the physiological information and specific stress level information associated with the specific audio content, wherein the specific stress level information comprises a first pulse rate of the user at the start of a previous play of the specific audio content and a second pulse rate of the user at the end of the previous play of the specific audio content, and wherein the at least one processor recommends the specific audio content based on a change in stress level of the user previously caused by the specific audio content as indicated by the specific stress level information.

2. The mobile terminal according to claim 1, wherein the at least one processor recommends the specific audio content before any content of the plurality of audio contents is played.

3. The mobile terminal according to claim 1, wherein the at least on processor is further configured to store in the memory the stress level information associated with each of the plurality of audio contents, the stress level information being acquired when each of the plurality of audio content is played prior to recommending the specific audio content.

4. The mobile terminal according to claim 3, wherein the at least one processor accesses the database when the physiological information has not been acquired by the at least one sensor, and recommends the audio content having a high play frequency.

5. The mobile terminal according to claim 1, wherein the at least one processor is further configured to determine a current stress level of the user on the basis of the physiological information acquired by the acquiring unit.

6. The mobile terminal according to claim 5, wherein the at least one processor further accesses the database when the current stress level is greater than a predetermined value, and recommends the specific audio content that changes the stress level.

7. The mobile terminal according to claim 1, wherein the database further associates behavioral information with each of the plurality of audio contents, and
   the at least one sensor is further configured to acquire the behavioral information; and
   the at least one processor is further configured to access the database on the basis of the physiological information and the behavioral information acquired by the at least one sensor, and search the memory for audio content to be recommended.

8. The mobile terminal according to claim 7, wherein the at least one processor searches for the audio content associated with the physiological information and the behavioral information that are similar to the physiological information and the behavioral information acquired by the at least one sensor, by referring to the database.

9. The mobile terminal according to claim 7, wherein the at least one sensor further detects an acceleration, wherein the behavioral information is based on the acceleration detected.

10. The mobile terminal according to claim 7, wherein the at least one processor, in a state where the physiological information cannot be acquired by the at least one sensor, refers to the database on the basis of the behavioral information acquired by the at least one sensor, and searches the memory for the audio content.

11. A mobile terminal, comprising:
   at least one sensor configured to acquire physiological information of a user of the mobile terminal when content is played on the mobile terminal;
   a memory that stores a plurality of contents and a database that associates past physiological information acquired by the sensor with the plurality of contents; and
   at least one processor that, when present physiological information is acquired by the at least one sensor, refers to the database and recommends a specific content from the plurality of contents, on the basis of the present physiological information and past physiological information associated with the specific content, wherein the database further associates past stress level information with each of the plurality of contents;
   wherein the at least one processor is configured to store past physiological and stress level information associated with each of the plurality of contents when each of the plurality of contents was previously played, wherein the stress level information associated with each of the plurality of contents comprises a first stress level of the user at the start of play of a content and a second stress level of the user at the end of play of the content; and
   wherein the at least one processor accesses the database when a current stress level of the user indicated by the present physiological information is greater than a predetermined value, and recommends a specific content from the plurality of contents based on a change in stress level of the user previously caused by the specific content as indicated by stress level information associated with the specific content.

* * * * *